(12) United States Patent
Sasayama et al.

(10) Patent No.: US 9,107,778 B2
(45) Date of Patent: Aug. 18, 2015

(54) DISPOSABLE WEARING ARTICLE

(75) Inventors: Kenichi Sasayama, Kanonji (JP);
Makoto Ichikawa, Kanonji (JP);
Kunihiko Katsuragawa, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 38 days.

(21) Appl. No.: 13/878,811

(22) PCT Filed: Jan. 27, 2012

(86) PCT No.: PCT/JP2012/000552
§ 371 (c)(1),
(2), (4) Date: Apr. 11, 2013

(87) PCT Pub. No.: WO2012/105212
PCT Pub. Date: Aug. 9, 2012

(65) Prior Publication Data
US 2013/0304011 A1    Nov. 14, 2013

(30) Foreign Application Priority Data

Jan. 31, 2011 (JP) .................................. 2011-019198
Dec. 2, 2011 (JP) .................................. 2011-265309

(51) Int. Cl.
*A61F 13/15* (2006.01)
*A61F 13/49* (2006.01)
*A61F 13/494* (2006.01)
*A61F 13/496* (2006.01)

(52) U.S. Cl.
CPC .......... *A61F 13/49019* (2013.01); *A61F 13/496* (2013.01); *A61F 13/49017* (2013.01); *A61F 13/49406* (2013.01); *A61F 13/49007* (2013.01); *A61F 2013/49025* (2013.01)

(58) Field of Classification Search
CPC ............ A61F 13/496; A61F 13/49017; A61F 13/4902; A61F 13/49022; A61F 13/49025; A61F 13/49007
USPC ............. 604/385.01, 385.22, 385.28, 385.29, 604/385.25, 385.24, 385.27, 385.26
See application file for complete search history.

(56) References Cited

U.S. PATENT DOCUMENTS

| 2009/0178755 A1 | 7/2009 | Hornung et al. |
| 2012/0077661 A1 | 3/2012 | Oonishi et al. |
| 2012/0191057 A1* | 7/2012 | Takino et al. ............ 604/385.29 |

FOREIGN PATENT DOCUMENTS

| CN | 101773432 A | 7/2010 |
| JP | 2004329238 A | 11/2004 |

(Continued)

OTHER PUBLICATIONS

International Search Report issued in PCT/JP2012/000552 on May 1, 2012.

*Primary Examiner* — Jacqueline Stephens
(74) *Attorney, Agent, or Firm* — Lowe Hauptman & Ham, LLP

(57) ABSTRACT

A disposable wearing includes a crotch chassis having a liquid-impervious sheet. The crotch chassis has a main region and opposite lateral portions lying outboard of the main region in the transverse direction and provided with leg elastic elements extending in the longitudinal direction. The opposite lateral portions respectively have fold lines extending in the longitudinal direction, outer side zones lying outboard of the respective fold lines in the transverse direction and inner side zones lying inboard of the respective fold lines in the transverse direction. The outer side zones of the respective lateral portions are folded inward and fixed to the associated inner side zones via associated bond zones extending in the longitudinal direction to form a pair of elastic lateral portions having folded back regions, respectively.

10 Claims, 13 Drawing Sheets

(56) References Cited

FOREIGN PATENT DOCUMENTS

| | | |
|---|---|---|
| JP | 2005270390 A | 10/2005 |
| JP | 2008302138 A | 12/2008 |
| JP | 2010017341 A | 1/2010 |
| JP | 2010240108 A | 10/2010 |
| WO | 2009080180 A1 | 7/2009 |
| WO | 2010113853 A1 | 10/2010 |
| WO | 2011039988 A1 | 4/2011 |

* cited by examiner

[Fig. 1]
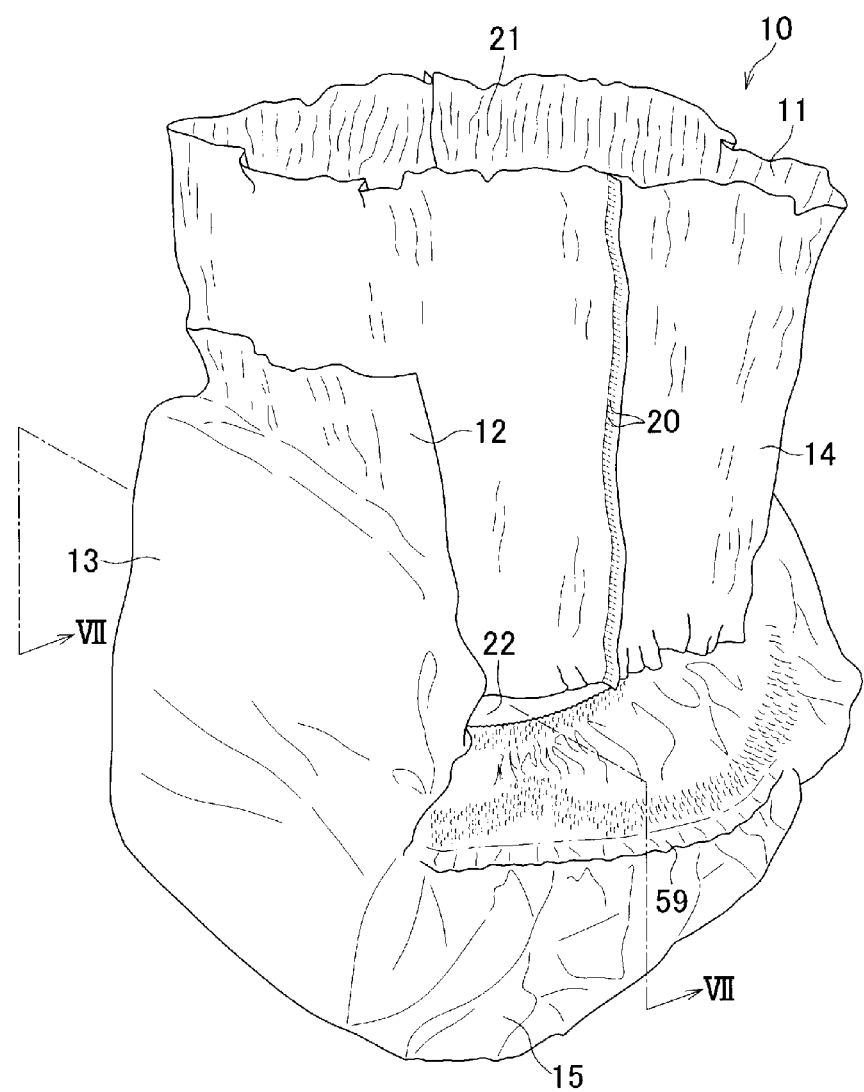

[Fig. 2]
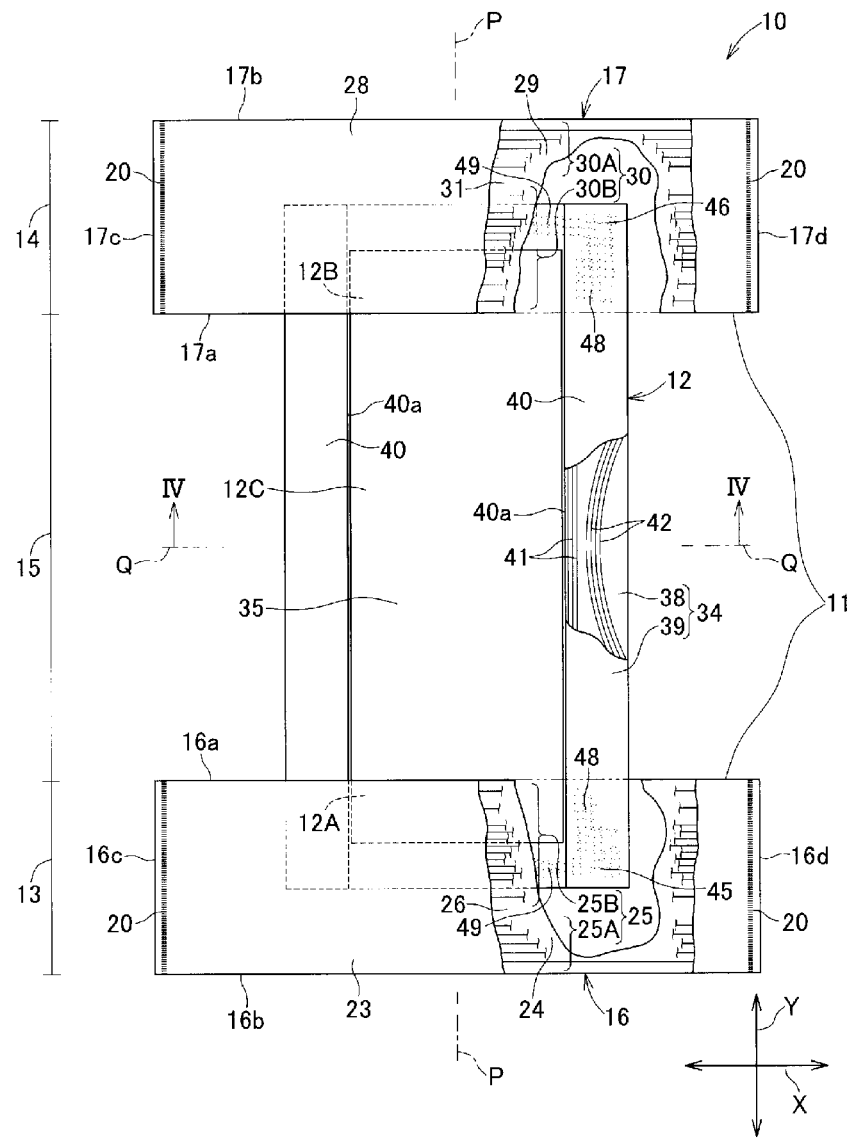

[Fig. 3]
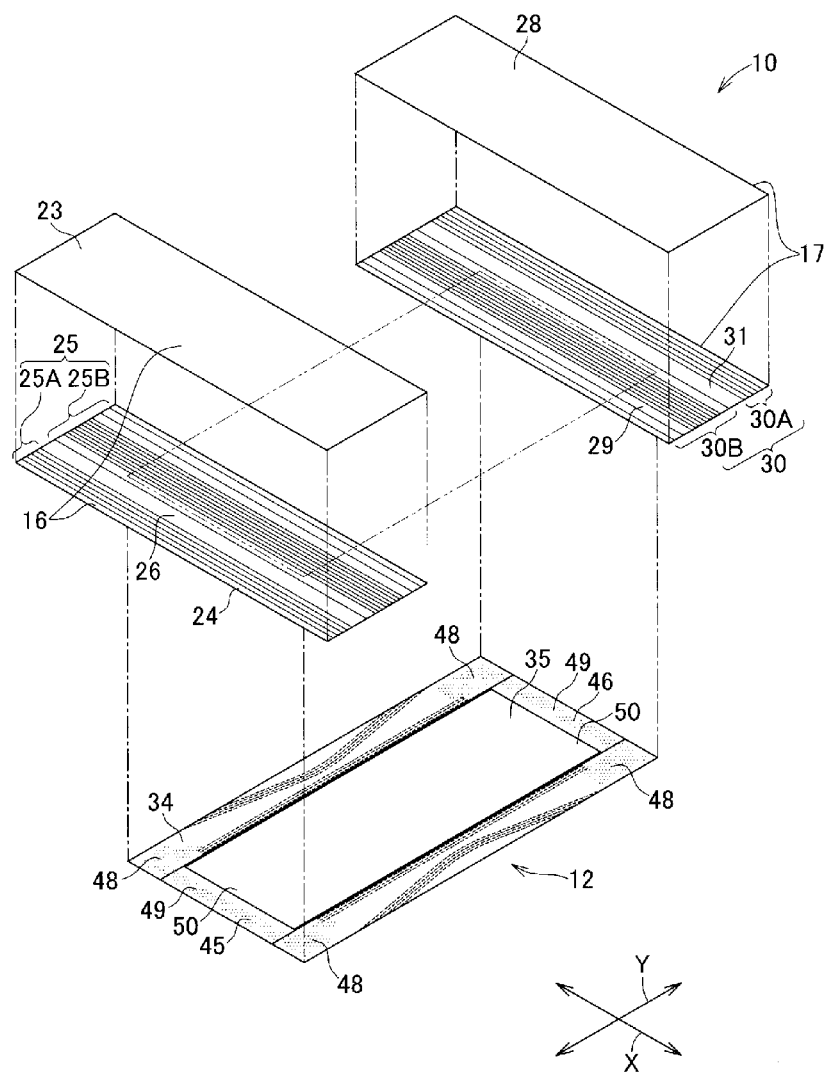
[Fig. 4]
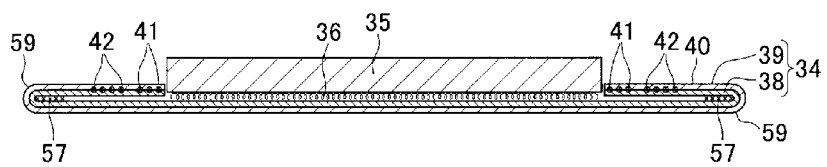

[Fig. 5]
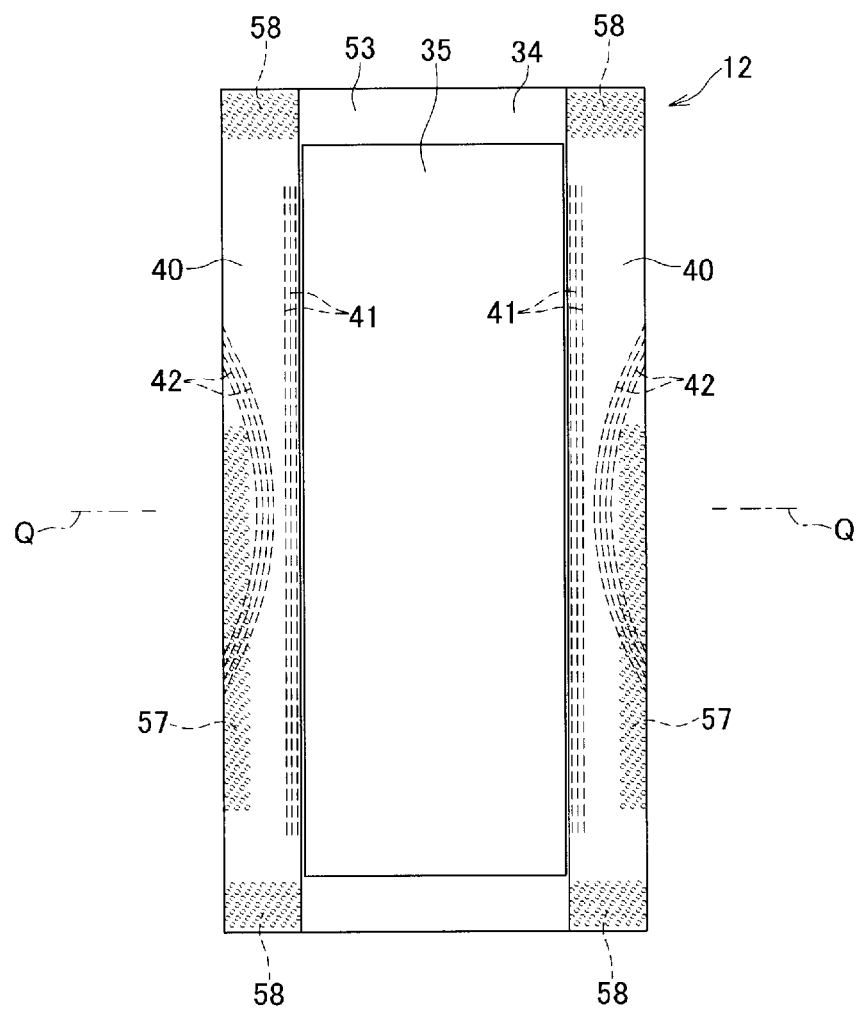

[Fig. 6]
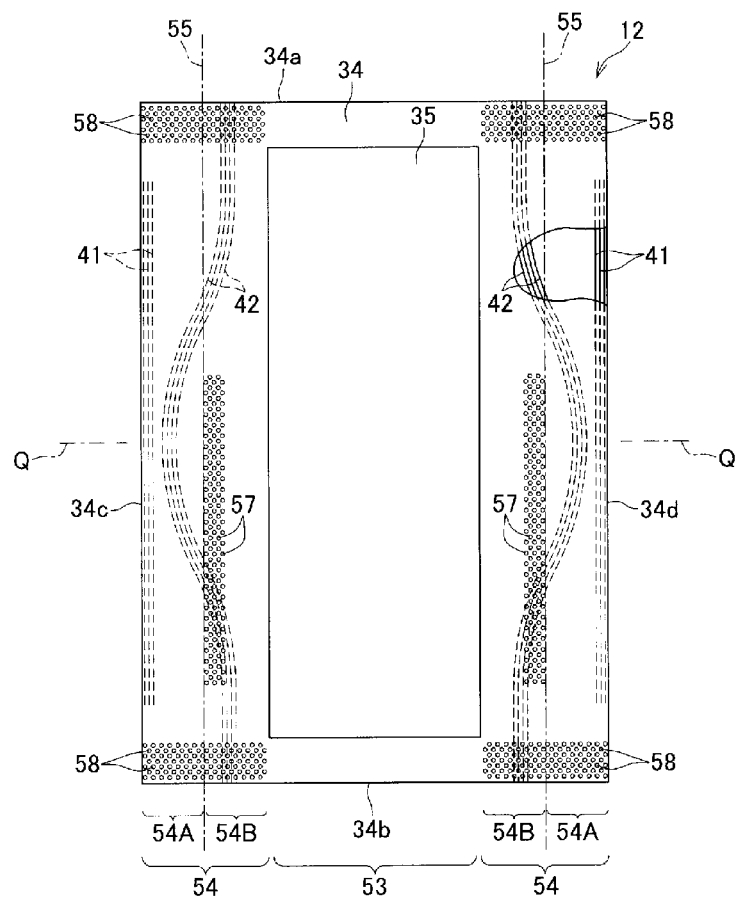
[Fig. 7]
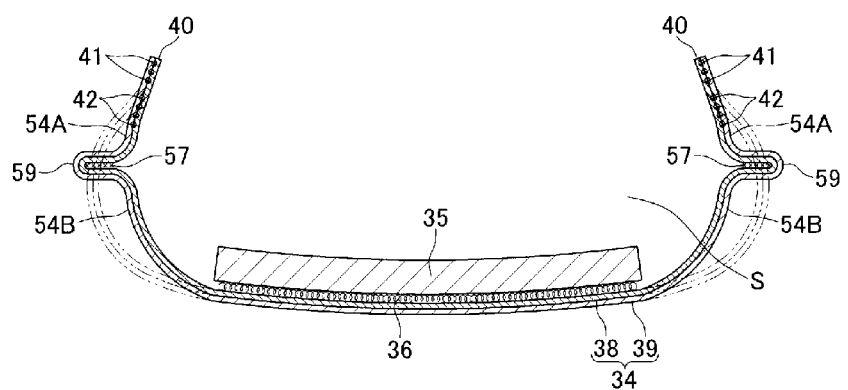

[Fig. 8]
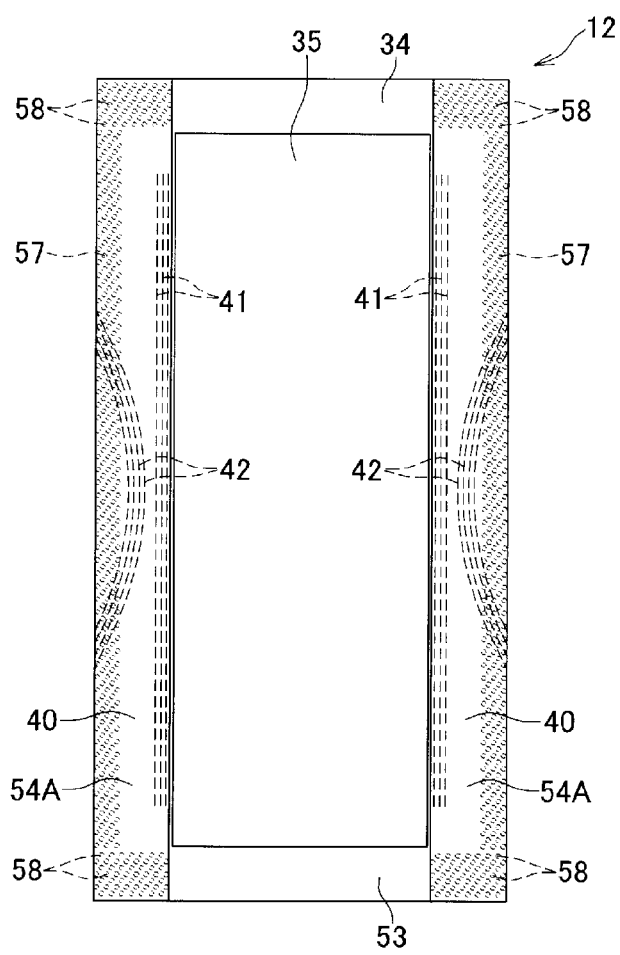

[Fig. 9]
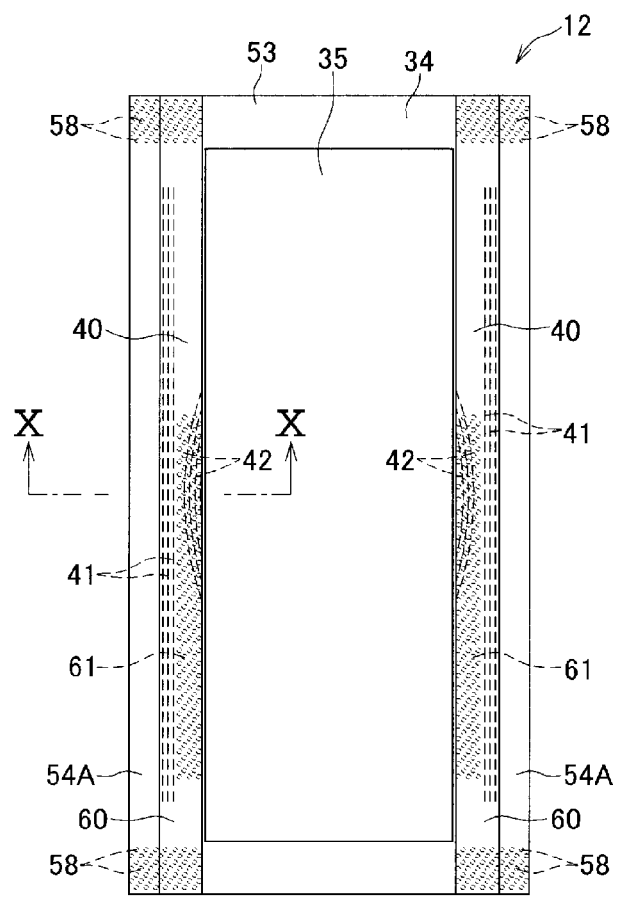
[Fig. 10]
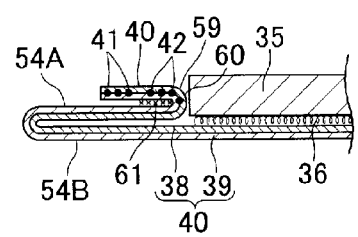

[Fig. 11]
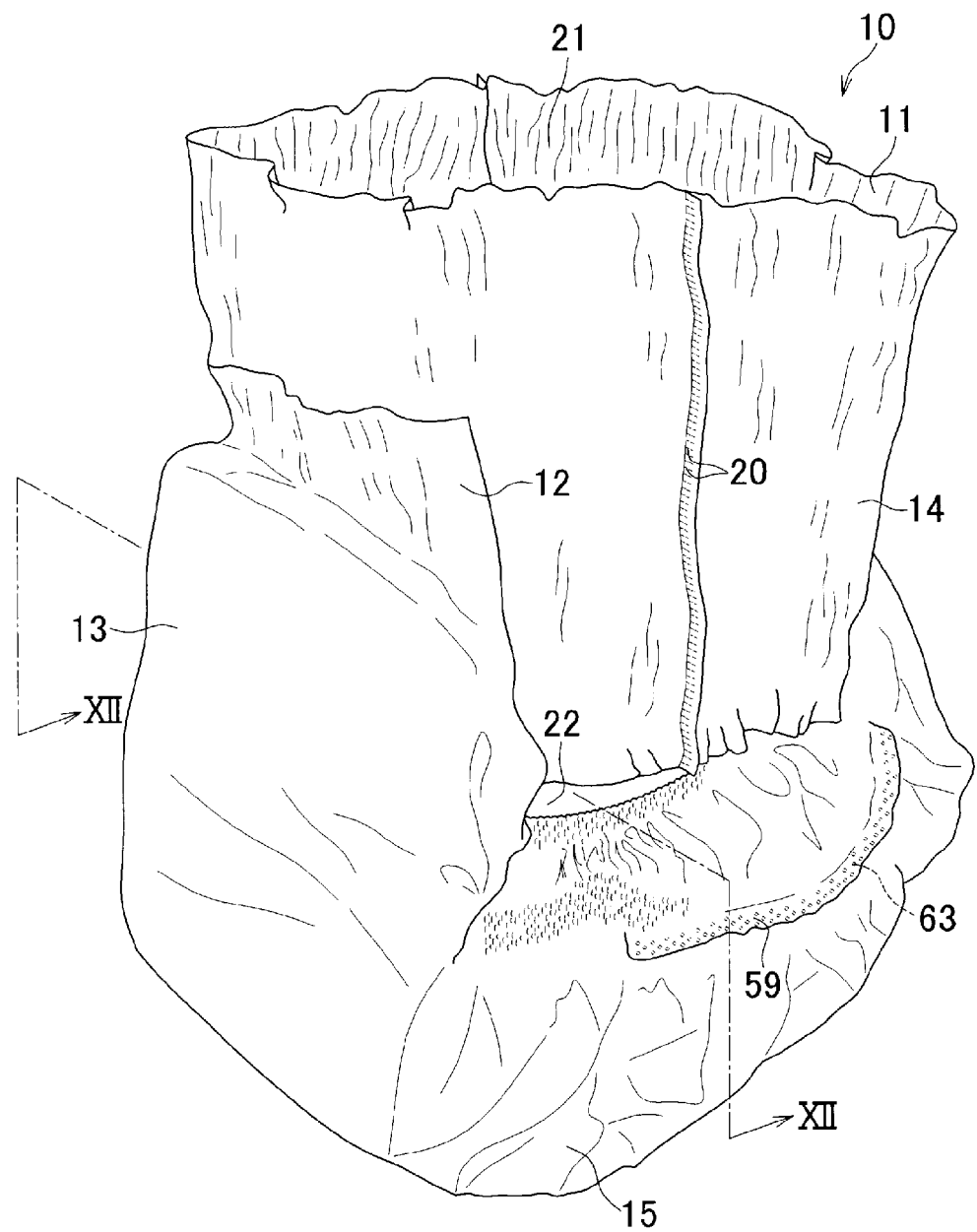

[Fig. 12]
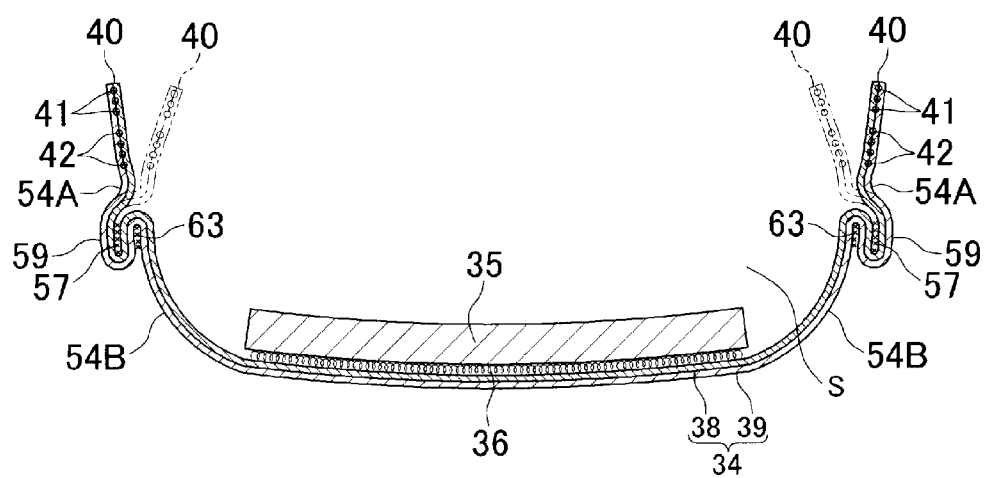

[Fig. 13]
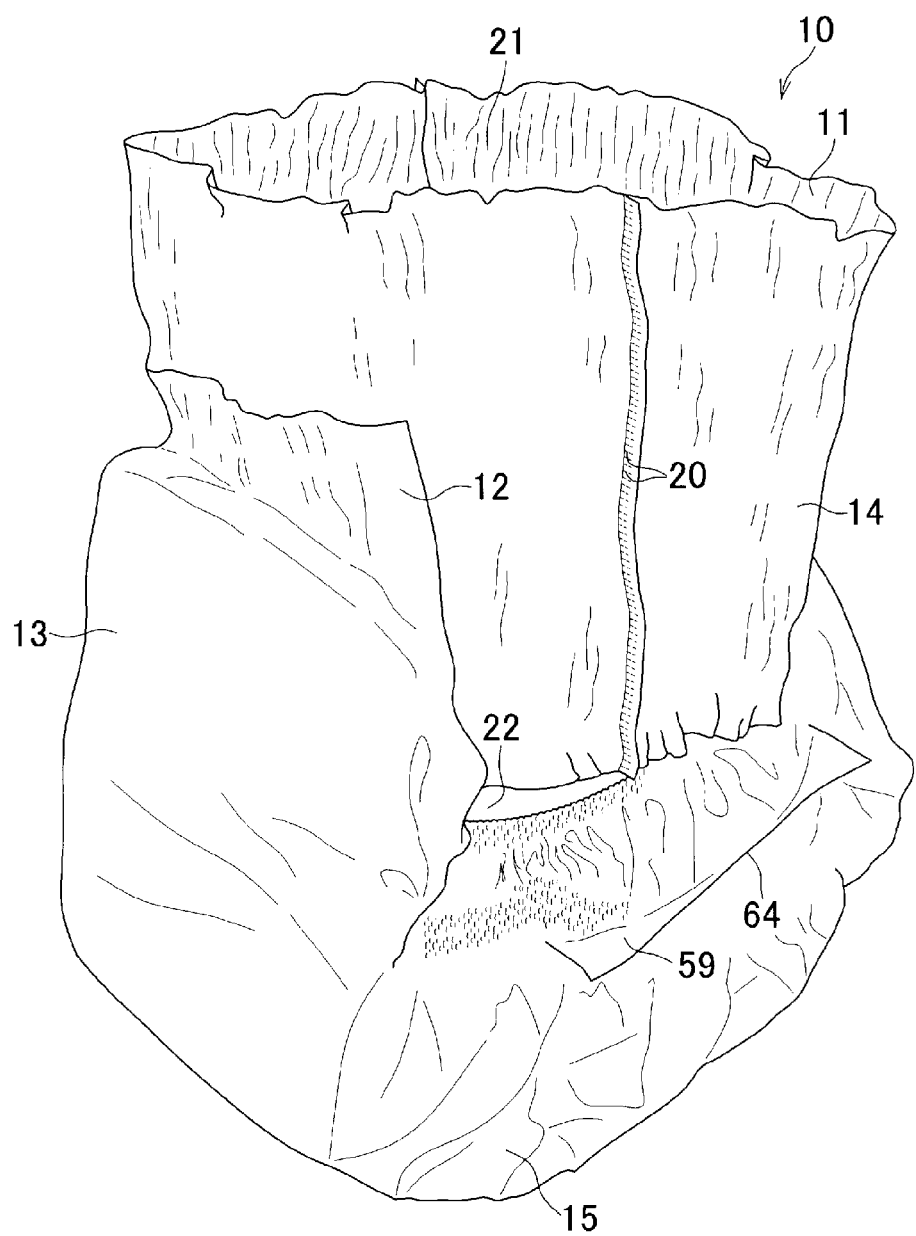

[Fig. 14]
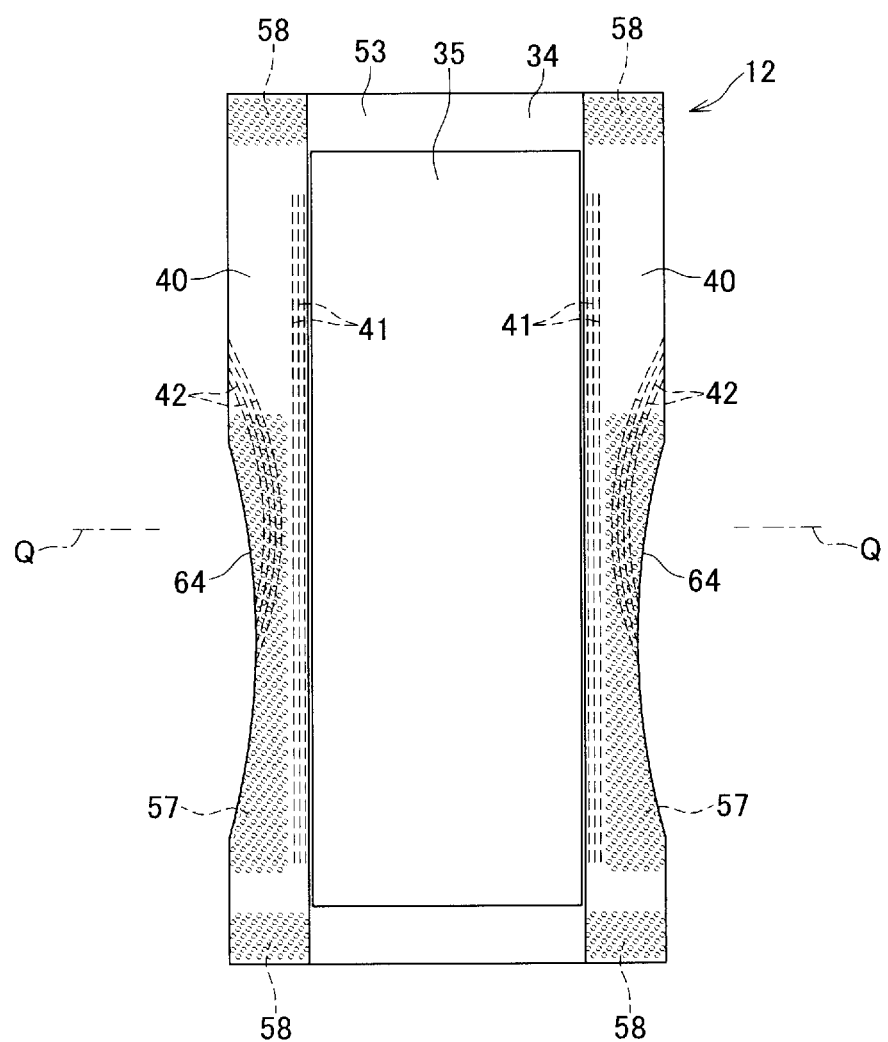

[Fig. 15]
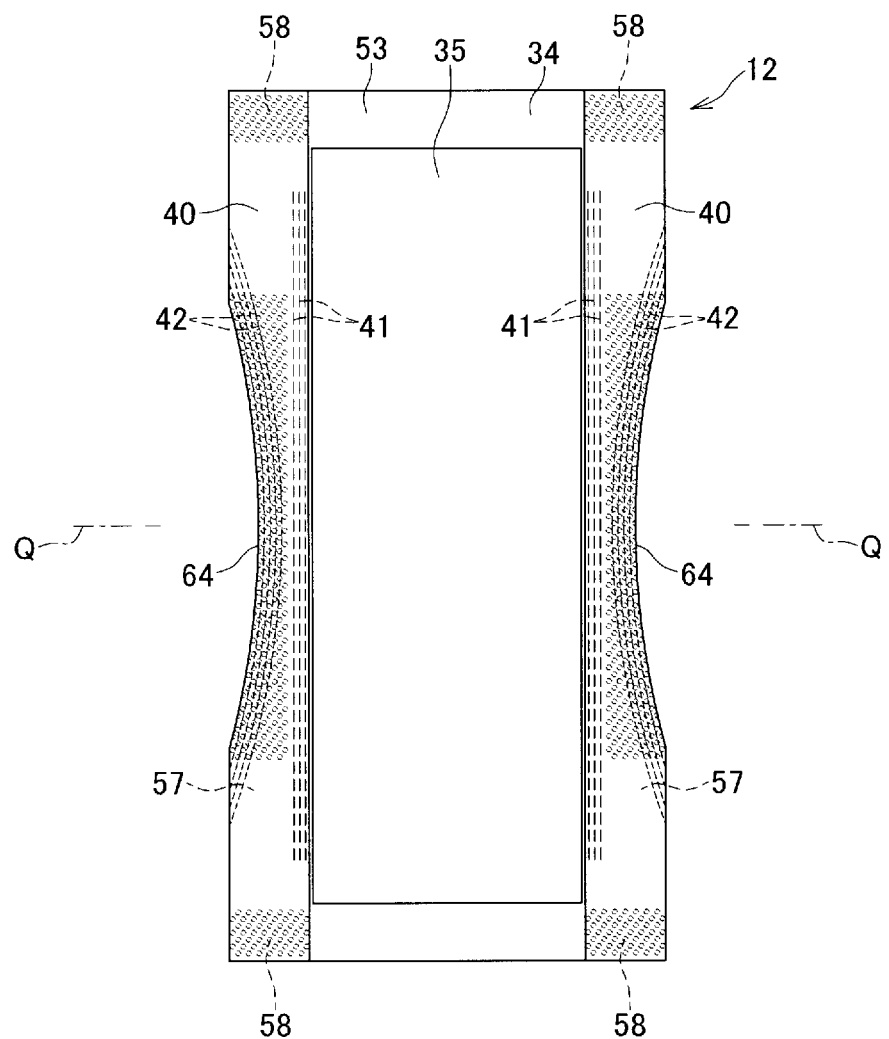

[Fig. 16]
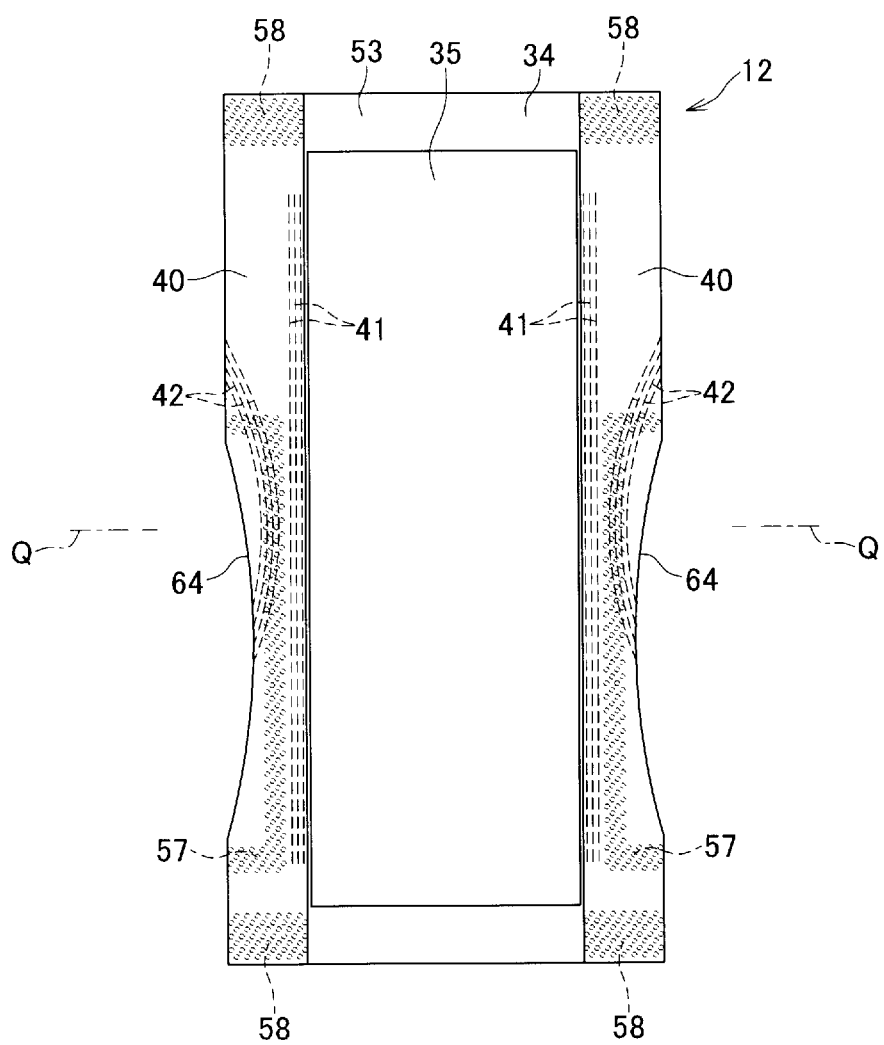

DISPOSABLE WEARING ARTICLE

RELATED APPLICATIONS

The present application is a National Phase of PCT/JP2012/000552, filed Jan. 27, 2012, and is based on, and claims priority from, Japanese Application No. 2011-019198, filed Jan. 31, 2011 and Japanese Application No. 2011-265309, filed Dec. 2, 2011.

TECHNICAL FIELD

This disclosure relates to disposable wearing articles and, more particularly, to disposable wearing articles such as disposable diapers, disposable toilet-training pants, disposable incontinent diapers and disposable menstruation pants each having an annular elastic waist panel and a crotch chassis attached thereto.

BACKGROUND

Conventionally, disposable diapers are known each having an annular elastic waist panel and a crotch chassis attached thereto. For example, PTL 1 discloses a disposable diaper including an elastic waist panel having a front waist panel defining a front waist region, a rear waist panel defining a rear waist region and a crotch chassis extending between the front and rear waist panels in a longitudinal direction and having front and end regions attached to the elastic waist panel.

CITATION LIST

Patent Literature

PTL 1: JP 2004-329238 A

SUMMARY

Technical Problem

In the disposable diaper disclosed in PTL 1, the front and rear end regions of the crotch chassis are interposed between respective inner and outer sheets of the front and rear waist panels and attached therebetween and the crotch chassis is provided along opposite lateral portions thereof with leg elastic elements extending in the longitudinal direction to define a pair of elastic lateral portions. With the diaper put on the wearer's body, the pair of the elastic lateral portions raise themselves toward the wearer's body to form between the front and rear waist panels and the crotch chassis a pocket adapted to collect the wearer's body waste. In this way, the crotch chassis is slung from the front and rear waist panels like a hammock so that a bodily waste collecting space for absorption and retention of a relatively large quantity of body waste is defined on the inner side of the crotch chassis.

The inventors have recognized that, in such disposable diaper, however, the elastic lateral portions may expand outward in a transverse direction of a bodily fluid absorbent structure beyond necessity with respect to the quantity of actually excreted body waste. In consequence, the wearer may be made uncomfortable and, in addition, the diaper may become visually unfavorable.

Solution to Problem

According to some embodiments of this invention, there is provided a disposable wearing article having a longitudinal direction, a transverse direction extending orthogonally to the longitudinal direction, comprising:
 a skin-facing side;
 a non-skin-facing side;
 a front waist region;
 a rear waist region; and
 a crotch region extending between the front and rear waist regions, and including an elastic waist panel defining the front and rear waist regions and a crotch chassis attached to the elastic waist panel to define respective portions of the front and rear waist regions and the crotch region.

In the disposable wearing article according to the present invention, the crotch chassis includes a liquid-impervious sheet having a main region and opposite lateral portions lying outboard of the main region in the transverse direction and provided with leg elastic elements extending in the longitudinal direction;
 the opposite lateral portions respectively have fold lines extending in the longitudinal direction, outer side zones lying outboard of the respective fold lines in the transverse direction and inner side zones lying inboard of the respective fold lines in the transverse direction; and
 the outer side zones of the respective lateral portions are folded back inward and fixed to the associated inner side zones via associated bond zones extending in the longitudinal direction to form a pair of elastic lateral portions having folded back regions, respectively.

BRIEF DESCRIPTION OF DRAWINGS

FIG. 1 is a perspective view of a disposable diaper as an example of the disposable wearing article according to a first embodiment of this invention.

FIG. 2 is a partially cutaway developed plan view of the diaper developed in a front-back direction after side seams of the diaper have been peeled off.

FIG. 3 is an exploded perspective view of the diaper.

FIG. 4 is a sectional view taken along line IV-IV in FIG. 2.

FIG. 5 is a plan view of a crotch chassis.

FIG. 6 is a developed plan view of a laminated crotch sheet.

FIG. 7 is a sectional view taken along line VII-VII in FIG. 1.

FIG. 8 is a plan view similar to FIG. 5, showing a second embodiment.

FIG. 9 is a plan view similar to FIG. 5, showing a third embodiment.

FIG. 10 is a sectional view taken along line X-X in FIG. 9.

FIG. 11 is a perspective view similar to FIG. 1, illustrating the diaper 10 according to the fourth embodiment.

FIG. 12 is a sectional view taken along line XII-XII in FIG. 11.

FIG. 13 is a perspective view similar to FIG. 1, illustrating the diaper 10 according to the fifth embodiment.

FIG. 14 is a plan view illustrating the crotch chassis according to the fifth embodiment.

FIG. 15 is a plan view illustrating the crotch chassis according to the sixth embodiment.

FIG. 16 is a plan view exemplarily illustrating the alternative crotch chassis according to the seventh embodiment.

DESCRIPTION OF EMBODIMENTS

First Embodiment

Referring to FIGS. 1 through 3, a disposable diaper 10 illustrated as an example of the disposable wearing article according to this invention has a longitudinal direction Y, a transverse direction X being orthogonal to the direction Y, imaginary longitudinal center line P-P bisecting a width dimension in the transverse direction X and imaginary transverse center line Q-Q bisecting a width dimension in the longitudinal direction Y.

The diaper 10 includes a skin-facing side, a non-skin-facing side opposed to the skin-facing side, an annular elastic waist panel 11 extending circumferentially around the wearer's waist and a crotch chassis 12 attached to the non-skin-facing side of the elastic waist panel 11, a front waist region 13 and a rear waist region 14 defined by the panels 11, 12, respectively, and a crotch region 15 extending in the longitudinal direction Y between the front and rear waist regions 13, 14.

The diaper 10 is configured symmetrically about imaginary center line P-P and the elastic waist panel 11 is composed of a front waist panel 16 lying in the front waist region 13 and a rear waist panel 17 lying in the rear waist region 14.

The front waist panel 16 is contoured by an inner end 16a extending across the crotch chassis 12 in the transverse direction X, an outer end 16b spaced from and opposed to the inner end 16a in the longitudinal direction Y and extending in the transverse direction X and both side edges 16c, 16d extending in the longitudinal direction Y between the inner and outer ends 16a, 16b to be shaped in a transversely long rectangle.

The rear waist panel 17 is generally the same as the front waist panel 16 in shape as well as in size and contoured by an inner end 17a extending across the crotch chassis 12 in the transverse direction X, an outer end 17b spaced from and opposed to the inner end 17a in the longitudinal direction Y and extending in the transverse direction X and both side edges 17c, 17d extending in the longitudinal direction Y between the inner and outer ends 17a, 17b in the longitudinal direction Y to be shaped in a transversely long rectangle.

The respective side edges 16c, 16d of the front waist panel 16 and the side edges 17c, 17d of the rear waist panel 17 are put flat and joined together by side seam lines 20 extending continually in the longitudinal direction Y to define a waist-opening 21 and a pair of leg-openings 22 (See FIG. 1). The side seam lines 20 may be provided by joint means of known art, for example, various types of heat sealing means such as hot embossing or ultrasonic processing treatment.

The front waist panel 16 includes a first inner sheet 23 lying on the skin-facing side and a first outer sheet 24 lying on the non-skin-facing side. The first inner and outer sheets may be respectively formed of a substantially liquid-impervious SMS (spunbonded/meltblown/spunbonded) fibrous nonwoven fabric or a spunbonded nonwoven fabric or a plastic sheet or a plastic sheet laminated with at least one of these nonwoven fabrics, each having a mass per unit area in a range of about 15 to about 30 g/m$^2$. The inner and outer sheets are bonded together with hot melt adhesives intermittently applied to the inner surface of one of these two sheets or heat sealing means.

A plurality of strand-like or string-like front waist elastic elements 25 extending in the transverse direction X are interposed between these two sheets 23, 24. The front waist panel 16 is contractibly elasticized at least in the transverse direction X under the effect of the front waist elastic elements 25. It is possible to bond the sheets 23, 24 together only with hot melt adhesives applied to substantially entire peripheral surfaces of the respective front waist elastic elements 25 provided that these sheets 23, 24 being bonded to each other should not be peeled off from each other in the course of handling the diaper 10 or during use thereof.

The front waist elastic elements 25 are composed of upper front waist elastic elements 25A extending along the outer end 16b of the front waist panel 16 in the transverse direction X and lower front waist elastic elements 25B extending along the inner end 16a in the transverse direction X. The lower front waist elastic elements 25B are arranged more closely than the upper front waist elastic elements 25A and an inelastic zone 26 including none of elastic elements is defined between the upper front waist elastic elements 25A and the lower front waist elastic elements 25B.

The rear waist panel 17 includes a second inner sheet 28 lying on the skin-facing side and a second outer sheet 29 lying on the non-skin-facing side. The second inner and outer sheets 28, 29 may be respectively formed of a substantially liquid-impervious SMS (spunbonded/meltblown/spunbonded) fibrous nonwoven fabric or a spunbonded nonwoven fabric or a plastic sheet or a plastic sheet laminated with these nonwoven fabrics, each having a mass per unit area in a range of about 15 to about 30 g/m$^2$. These two sheets 28, 29 are bonded together with hot melt adhesives intermittently applied to the inner surface of one of these two sheets or by the heat sealing means.

A plurality of strand-like or string-like rear waist elastic elements 30 extending in the transverse direction X are interposed between these two sheets 28, 29. The rear waist panel 17 is contractible at least in the transverse direction X under the effect of the rear waist elastic elements 30. It is possible to bond these two sheets 28, 29 together only with hot melt adhesives applied to generally entire peripheral surfaces of the respective rear waist elastic elements 30 provided that these sheets 28, 29 being bonded to each other should not be peeled off from each other in the course of handling the diaper 10 or during use thereof.

The rear waist elastic elements 30 consist of upper rear waist elastic elements 30A extending along the outer end 17b of the rear waist panel 17 in the transverse direction X and lower rear waist elastic elements 30B extending along the lower end 17a in the transverse direction X. The lower rear waist elastic elements 30B are arranged more closely than the upper rear waist elastic elements 30A and an inelastic zone 31 including none of the elastic elements is defined between the upper rear waist elastic elements 30A and the lower rear waist elastic elements 30B.

The crotch chassis 12 has a substantially rectangular shape which is vertically long and includes a front end segment 12A attached to the non-skin-facing side of the front waist panel 16 (i.e., outer surface), a rear end segment 12B attached to the non-skin-facing side of the rear waist panel 17 and intermediate segment 12C extending in the longitudinal direction Y between the front and rear segments 12A, 12B. The crotch chassis 12 further includes a laminated crotch sheet 34 and a bodily fluid absorbent structure 35 placed on the skin-facing side of the laminated crotch sheet 34 (i.e., inner surface). The laminated crotch sheet 34 and the bodily fluid absorbent structure 35 are bonded to each other with hot melt adhesive 36 intermittently applied to these opposite inner surfaces.

The bodily fluid absorbent structure 35 may be formed by wrapping a liquid-absorbent core containing SAP (Superabsorbent Polymer Particles) molded in a pad-shape with a liquid-dispersant sheet. More specifically, the liquid-absorbent core, a hydrophilic nonwoven fabric lying on the upper surface of the liquid-absorbent core and having a mass per unit area of about 10 g/m$^2$ and an SMS fibrous nonwoven fabric lying on the bottom surface of the liquid-absorbent core and having a mass per unit area of about 11 g/m$^2$ may be stacked one on another and intermittently bonded one to another with hot melt adhesive to form the bodily fluid-absorbent structure 35. The bodily fluid absorbent structure formed only by SAP and the wrapping sheet used to wrap this SAP in this manner is correspondingly thinner than the conventional structure formed by a mixture of SAP and fluff pulp and consequently can smoothly conform to the movement of the crotch chassis 12.

Specifically, thickness of the crotch chassis 12 including the bodily fluid absorbent structure 35 at its midsection thereof is less than about 5.0 mm. A cantilever bending resistance thereof is in a range of about 15 to about 140 mm.

<Thickness Measuring Method>

Thickness of the crotch chassis 12 in its midsection may be measured by (PEACOCK) Thickness Tester of OZAKI MFG CO. LTD. (a probe diameter is in a range of about 10 to about 20 mm).

<Cantilever Bending Resistance Measuring Method>

In accordance with the cantilever method prescribed by JIS L 1096, test pieces (each having a length dimension of about 50 mm in the transverse direction X and a length dimension of about 150 mm in the longitudinal direction Y) are cut out from the midsection of the crotch chassis 12 of the diaper 10 and the cantilever bending resistance is measured on the skin-facing side and on the non-skin-facing side for the respective test pieces. The number of times (n) measurement is repeated on the respective test pieces is set to 3.

The laminated crotch sheet 34 is formed of inner crotch sheet 38 and outer crotch sheet 39 at least one of which is formed of a liquid-impervious fibrous nonwoven fabric sheet or a plastic film. The inner and outer crotch sheets 38, 39 are bonded to each other with hot melt adhesive (not shown) applied to the inner surface of one of these both sheets 38, 39 and respective opposite lateral portions are folded inward to form a pair of elastic lateral portions 40 extending in the longitudinal direction.

Each of the elastic lateral portions 40 is provided with a plurality of strand-like or string-like first leg elastic elements 41 and second leg elastic elements 42 both extending in the longitudinal direction Y and thereby the lateral portions 40 are elasticized at least in the longitudinal direction Y. The first leg elastic elements 41 are formed of a plurality of elastic elements rectilinearly extending in the longitudinal direction Y along inner side edges of the respective elastic lateral portions 40, and the second leg elastic elements 42 are formed of a plurality of elastic elements convexly curving toward the longitudinal axis P in the midsection of the crotch region 15 and extending along the circumference of the wearer's thighs. The first and second leg elastic elements 41, 42 are interposed and affixed between the inner and outer crotch sheets 38, 39 with hot melt adhesives (not shown).

Under the effect of the first and second leg elastic elements 41, 42 arranged in such manner, the crotch chassis 12 takes the form of a hammock slung from the elastic waist panel 11 and a body waste collecting space S is defined inside the crotch chassis 12 (See FIG. 7). The crotch chassis 12 being slung to be spaced from the wearer's buttocks in this manner advantageously makes it possible to absorb and to contain a relatively large quantity of body waste and, at the same time, makes it possible to restrict a possibility that the wearer's buttocks might be soiled with body waste discharged onto the crotch chassis 12.

Referring to FIGS. 2 and 3, at a front bond zone 45 and a rear bond zone 46 defined by coating the respective skin-facing sides of the front end segment 12A and the rear end segment 12B with hot melt adhesives, the crotch chassis 12 is attached to the respective outer surfaces of the front and rear waist panels 16, 17. By attaching the front and rear end segments 12A, 12B of the crotch chassis 12 to the respective outer surfaces of the front and rear waist panels 16, 17 in this manner, it is assured to form the body waste collecting space S of a sufficiently large volume. Provided that the body waste collecting space S has a desired volume, it is possible to attach one of the front and rear end segments 12A, 12B to the outer surface of the front waist panel 16 or the rear waist panel 17 and to attach the other to the inner surface of the front or rear waist panel 16 or 17.

Each of the front and rear bond zones 45, 46 is generally U-shaped to open toward the crotch region 15 and includes both lateral portions 48 formed by coating the skin-facing side of the elastic lateral portions 40 with hot melt adhesives and a middle zone 49 extending in the transverse direction X between the both lateral portions 48. The middle zone 49 lies outboard of the area occupied by the bodily fluid absorbent structure 35 as viewed in the longitudinal direction Y and, between the lateral portions 48 and the middle zone 49, a non-bond zone 50 not coated with hot melt adhesive. While each of the lateral portions 48 in the front bond zone 45 has a stepped shape and each of the lateral portions 48 in the rear bond zone 46 has a rectangular shape in this embodiment, the lateral portions 48 of the front and rear bond zones 45, 46 are not limited to these shapes but may be selected from a group including a stepped shape, a rectangular shape, a curved shape and others.

Referring to FIGS. 4 through 6, the elastic lateral portions 40 and a main region 53 occupied by the bodily fluid absorbent structure 35 in the laminated crotch sheet 34 are bonded together via a bond zone interposed therebetween and coated with hot melt adhesives. It should be appreciated that lateral bond zones 57 and end segment bond zones 58 lying within the laminated crotch sheet 34 are indicated by imaginary lines for convenience of illustration in FIG. 5 and the front and rear bond zones 45, 46 lying on the skin-facing side of the laminated crotch sheet 34 are not shown in FIGS. 5 and 6. More specifically, the laminated crotch sheet 34 has a rectangular shape in its opened state as will be apparent from FIG. 6 and this rectangular shape is contoured by opposite ends 34a, 34b rectilinearly extending in the transverse direction X in parallel to each other and opposite side edges 34c, 34d rectilinearly extending in the longitudinal direction in parallel to each other. The laminated crotch sheet 34 includes the main region 53 and opposite lateral portions 54 lying on both sides of the main region 53 in the transverse direction X thereof wherein the respective lateral portions 54 are formed with fold lines 55 bisecting a width dimension of the respective lateral portions 54. The respective lateral portions 54 are divided into outer side zones 54A lying outboard of the respective fold lines 55 in the transverse direction X and inner side zones 54B lying inboard of the respective fold lines 55.

The laminated crotch sheet 34 is formed on its inner surface with lateral bond zones 57 extending in the longitudinal direction Y along the fold lines 55 and end region bond zones 58 extending inward along the opposite ends 34a, 34b from the opposite side edges 34c, 34d of the laminated crotch sheet 34 (i.e., inner side edges 40a of the respective elastic lateral portions 40). The outer side zones 54A of the opposite lateral portions 54 may be folded inward along the associated fold lines 55 and may be bonded to the inner side zones 54B opposed to the respective outer side zones 54A via the lateral bond zones 57 and the end region bond zones 58 to form the elastic lateral portions 40. Provided that the elastic lateral portions 40 can be formed by folding the lateral portions 54 inward, at least the lateral bond zones 57 of the lateral bond zones 57 and the end region bond zones 58 may be formed to achieve the desired effect.

Referring to FIG. 7, in the elastic lateral portions 40, the laminated crotch sheet 34 is partially folded back inward and bonded to itself and thereby folded back regions 59 are formed. In consequence, elastic lateral portions 40 should not bow and the crotch chassis might expand in the transverse direction X beyond the necessity even when the first and second leg elastic elements 41, 42 are stretched in the diaper 10 put on the wearer's body. It should be appreciated here that in FIG. 7, a sectional view supposed for the case in which the elastic lateral portions 40 are neither partially folded nor bonded is indicated by imaginary lines. As indicated by the imaginary lines in FIG. 7, assumed that the laminated crotch sheet 34 is not partially fixed via the lateral bond zones 57 and the end region bond zones 58, the elastic lateral portions 40 as a whole will be spaced from the main region 53 as the first and second leg elastic elements 41, 42 are stretched. In addition, the front and rear end segments 12A, 12B of the crotch chassis 12 are attached to the respective outer surfaces of the front and rear waist panels 16, 17. In consequence, the crotch chassis 12 takes the form like a hammock having a relatively large body waste collecting capacity.

With this assumed arrangement, the body waste collecting space S of a relatively large volume is defined in this manner and a correspondingly large quantity of body waste can be absorbed and contained. However, the laminated crotch sheet 34 is formed by the flexible sheet member alone and, in consequence, the elastic lateral portions 40 excessively bulge outward from the both side edges of the bodily fluid-absorbent structure 35 in the transverse direction X beyond necessity for a quantity of body waste actually discharged. If the wearer having such diaper put on wearer's body gets dressed, such diaper will create an uncomfortable feeling of stiffness against the wearer and the wearer's figure will be made visually unfavorable. Particularly when, in this assumed case, the bodily fluid-absorbent structure 35 is formed to be relatively thin as in this embodiment of the invention, the bodily fluid-absorbent structure 35 will be curved together with the elastic lateral portions 40, resulting in a high likelihood of such problem.

In contrast, according to this embodiment of the invention, the laminated crotch sheet 34 is partially formed with folded back region 59 so that the elastic lateral portions 40 may raise themselves toward the wearer's body substantially upright without the anxiety that the bodily fluid-absorbent structure 35 might excessively expand in the transverse direction X. In this way, the elastic lateral portions 40 serve as leakage-barriers adapted to prevent bodily fluids from leaking sideways, and the wearer can get free of any discomfort feeling due to stiffness of the elastic lateral portions and project a visually neat impression.

As will be apparent from FIG. 6, the lateral bond zones 57 are preferably deviated toward the front waist region 13 about a transverse axis Q. With the diaper 10 put on the wearer's body, the segments of the lateral bond zones deviated toward the front waist region 13 are positioned to face the wearer's thighs and three-dimensional shapes defined by the segments of the respective elastic lateral portions 40 lying on the front waist region 13 are more compact than the segments lying on the rear waist region 14. In consequence, even when the wearer's thighs move, these segments would not create an uncomfortable feeling of stiffness against the wearer. In addition, the wearer may project a visually neat impression and, as a result, an exterior appearance of the diaper 10 from the front may be improved.

Referring to FIGS. 4 and 5, the lateral bond zones 57 lie outboard of the first and second leg elastic elements 41, 42 in the longitudinal midsection of the crotch region 15. With such arrangement, there is no disadvantageous possibility that the lateral bond zones 57 might be contracted and have stiffness increased under the elastic force of these elastic elements 41, 42 with a result that the intrinsic texture of the sheets in these zones 57 might be deteriorated. Referring to FIG. 5, a length dimension of the respective elastic lateral portions 40 in the transverse direction X is preferably in a range of about 20 to about 100 mm and a length dimension of the respective lateral bond zones 57 in the transverse direction X is preferably in a range of about 10 to about 90% of a length dimension of the respective outer side zones 54A in the respective elastic lateral portions 40.

As has been previously described, the laminated crotch sheet 34 is formed by the laminate comprising of the inner crotch sheet 38 and the outer crotch sheet 39 each defining the outer surface of the crotch chassis 12 and therefore there is no possibility that body waste might leak out beyond the outer side edges of the elastic lateral portions 40 (i.e., the fold lines 55 of the crotch laminate sheet). It is possible to form both the inner crotch and outer sheets 38, 39 of a thermoplastic resin film to reduce a quantity of hot melt adhesive used for the respective bond zones of the crotch chassis 12 in comparison to the case in which one of the inner and outer sheets 38, 39 is formed of a fibrous nonwoven fabric sheet. It is also possible, so far as the effect of this invention can be expected, to define the three-dimensional structure of the crotch chassis 12 by forming the elastic lateral portions 40 of a sheet member prepared separately of the sheet members forming the main region 53 and bonding them via the respective bond zones rather than forming the elastic lateral portions 40 and the main region 53 by a continuous single- or a multilayered sheet member. Furthermore, length dimensions of the inner and outer crotch sheets 38, 39 in the transverse direction X may be differentiated. For example, when the length dimension of the outer crotch sheet 39 in the transverse direction X is larger than that of the inner crotch sheet 38, the transverse extensions thereof may be folded inward to form sleeves adapted to prevent the first leg elastic elements 41 from being left out from the laminated crotch sheet 34.

Of the inner and outer crotch sheets 38, 39, at least the inner crotch sheet 38 is preferably formed by thermoplastic resin film. This is because when the inner crotch sheet 38 is formed of a thermoplastic resin film, the bonded surfaces in the lateral bond zones 57 as well as in the end segment bond zones 58 are formed of a thermoplastic resin film, sufficient joint strength can be assured even if an application quantity of hot melt adhesive in each of the bond zones is insufficient for the case in which one or both of the bonded surfaces is or are formed of a fibrous nonwoven fabric. Specifically, in the case of the end segment bond zones 58 formed of a thermoplastic resin film, a mass per unit area of hot melt adhesive to be applied to the lateral bond zones 57 and the end segment bond zones 58 may be in a range of about 1 to about 15 g/m².

The application pattern for each of the bond zones may be selected from various application patterns of known art such as a spiral pattern, an omega-pattern, a random linear pattern and a dotted pattern. Depending on a joint area of each bond zone and a kind of the sheet to be used, the mass per unit area of hot melt adhesive, for example, in the bond zones in which the inner and outer crotch sheets 38, 39 forming the laminated crotch sheet are bonded to each other may be in a range of about 1.0 to about 15.0 g/m².

Second Embodiment

This embodiment will be described hereunder exclusively with respect to the features distinguished from those of the first embodiment with reference to FIG. 8. According to this embodiment, the lateral bond zones 57 fully extend in the longitudinal direction Y of the crotch chassis 12. These lateral bond zones 57 fully extending in the longitudinal direction Y of the crotch chassis 12 serve to prevent the elastic lateral portions 40 from expanding outward in the transverse direction X and, at the same time, allow the outer side zones 54A of the respective elastic lateral portions 40 to raise themselves substantially upright toward the wearer's body on the respective bond zones.

Third Embodiment

This embodiment will be described hereunder exclusively with respect to the features distinguished from those of the first embodiment with reference to FIGS. 9 and 10. According to this embodiment, the outer side zones 54A of the respective elastic lateral portions 40 are folded outward to define folded zones 60 of which respective inner surfaces are bonded to portions of the elastic lateral portions 40 facing these inner surfaces via flap bond zones 61. By folding the elastic lateral portions 40 outward and fixing them in this state, the length dimension of the respective elastic lateral portions 40 in the transverse direction X can be further reduced and thereby the undesirable expansion outward thereof in the transverse direction X can be reliably prevented.

Fourth Embodiment

This embodiment will be described hereunder exclusively with respect to the features distinguished from those of the first embodiment in reference to FIGS. 11 and 12. According to this embodiment, respective halves (lower halves) of the folded back regions 59 are fixed to respective transversely inner side zones 54B of the laterals 54 of the laminated crotch sheet 34 by means of bond zones 63. In the respective bond zones 63, sections of the sheet facing to each other bonded together by means of appropriate adhesive such as hot melt adhesives or fusion bonded together by means of heat or ultrasonic emboss-working of known art. With the respective folded back regions 59 fixed in this manner, the transversely outer side zones 54A of the laterals 54 move outward as indicated by imaginary lines from the respective positions before the respective folded back regions 59 have been fixed by means of the respective bond zones 63. Consequently, a body waste receiving space S defined by the crotch chassis 12 can be broadened. In the case of the first embodiment, there is an anxiety that the folded back regions 59 projecting outward might be caught by the wearer's thighs and prevent smooth handling to put the diaper 10 on the wearer's body or uncomfortably irritate the wearer's skin in the course of guiding the wearer's legs through the leg-openings 22. Such disadvantage can be eliminated, according to this embodiment, by fixing the folded back regions 59. Each of the bond zones 63 may be provided on any one of the lower surface and the upper surface of the respective folded back regions 59.

Fifth Embodiment

This embodiment will be described hereunder exclusively with respect to the features distinguished from those of the first embodiment in reference to FIGS. 13 and 14. According to this embodiment, outer side edges 64 of the respective folded back regions 59 are cut off so that newly defined outer side edges may concavely curve outward. By cutting off the outer side edges 64 of the respective folded back regions 59 so as to curve concavely outward, the length dimension in the transverse direction X between the outer side edges 64 of the respective folded back regions 59 is correspondingly reduced. In consequence, it is possible not only to prevent the wearer's legs from being caught by the folded back regions 59 in the course of guiding the wearer's legs through the leg-openings 22 but also to improve fitness feeling by contours of the respective outer side edges so as to curve along the wearer's thighs. In addition, while it is apprehended that the folded back regions 59 might function like ribs to increase stiffness of the elastic lateral portions 40 and to restrict outward expansion of the elastic lateral portions 40 when body waste is received in the body waste receiving space S, it is possible to reduce stiffness of the elastic lateral portions 40 as a whole by partially cutting off the folded back regions 59.

Sixth Embodiment

This embodiment will be described hereunder exclusively with respect to the features distinguished from those of the first embodiment in reference to FIG. 15. According to this embodiment, the second leg elastic elements 42 are arranged so as to have relatively gentle curvature over relatively wide range and the folded back regions 59 are partially cut off so as to curve concavely outward without cutting the second leg elastic elements 42. By partially cutting off the folded back regions 59 so as to curve concavely, the length dimension in the transverse direction X between the outer side edges 64 of the respective folded back regions 59 are correspondingly reduced. As a consequence, it is possible to prevent the wearer's legs might be caught by the folded back regions 59 in the course of guiding the wearer's legs through the leg-openings 22 and additionally to improve a feeling of the fitness to the wearer's thighs. This embodiment is distinguished from the fifth embodiment in that none of the second leg elastic elements 42 is cut off together with the base sheet. Therefore, there is no anxiety that the cut edges of the leg elastic elements 42 might come in contact with the wearer's thighs and uncomfortably irritate the thighs and/or the leg elastic elements 42 might be partially exposed outward from the elastic lateral portions 41.

Seventh Embodiment

Referring to FIG. 16, the respective lateral bond zones 57 of the laminated crotch sheet 34 are respectively shaped so as to curve concavely outward and outer side edges 64 of the sections surrounded by the respective lateral bond zones 57 are cut off so as to curve concavely outward. Also in this manner, it is possible to form the folded back regions 59 having the outer side edges 64 shaped to curve concavely outward as illustrated in FIG. 13. In the cases of the fifth and sixth embodiments illustrated in FIGS. 14 and 15, respectively, the lateral bond zones 57 stiffened due to hot melt adhesives applied thereto are cut off and, therefore, there is an anxiety that the outer side edges 54 might come in contact directly with the wearer's thighs and uncomfortably irritate the thighs even if the outer side edges 54 are shaped so as to curve in consideration of fitness. According to this embodiment, the lateral bond zones 57 are spaced from the associated outer side edges 64 by a predetermined dimension and, as an advantageous consequence, there is no anxiety that the lateral bond zones 57 having relatively high stiffness might come in contact directly with the wearer's skin. In this way, texture can be further improved. In addition, the lateral bond zones 57 have concave shapes and, even if the sections surrounded by these lateral bond zones 57 are cut off, there is no apprehension that body waste once received might leak out from the body waste receiving space S.

The component members of the diaper 10 are not limited to those described in this specification but the other various types of material widely used in the relevant technical field may be used without limitation. The terms "first" and "second" used in the specification and claims of the present invention are used merely to distinguish the similar elements, similar positions or the other similar means.

The first aspects described above may be arranged in at least the following item:

(i) A disposable wearing article has a longitudinal direction, a transverse direction extending orthogonally to the longitudinal direction, and includes a skin-facing side, a non-skin-facing side, a front waist region, a rear waist region and a crotch region extending between the front and rear waist regions, an elastic waist panel defining the front and rear waist regions and a crotch chassis attached to the elastic waist panel to define respective portions of the front and rear waist regions and the crotch region, wherein:

the crotch chassis includes a liquid-impervious sheet having a main region and opposite lateral portions lying outboard of the main region in the transverse direction and provided with leg elastic elements extending in the longitudinal direction;

the opposite lateral portions respectively have fold lines extending in the longitudinal direction, outer side zones lying outboard of the respective fold lines in the transverse direction and inner side zones lying inboard of the respective fold lines in the transverse direction; and the outer side zones of the respective lateral portions are folded inward and affixed to the associated inner side zones via associated bond zones extending in the longitudinal direction to form a pair of elastic lateral portions.

The aspect described in the above item (i) may provide one or more of the following advantageous effects:

(a) The disposable wearing article according to this invention is similar to some of the conventional disposable wearing articles in the aspect that the crotch chassis is attached to the outer surface of the elastic waist panel and thereby a relatively large collecting space for body waste is assured but clearly distinguished from those of prior art in that the liquid-impervious sheet of the paired elastic lateral portions is partially tucked to form the folded leaves adapted to prevent the crotch chassis from expanding in the transverse direction beyond necessity and thereby to make the article wearer to project a visually neat impression.

The aspect described in the above item (i) may include one or more of the following embodiments:

(ii) The liquid-impervious sheet is a laminated crotch sheet composed of an inner crotch sheet lying on the skin-facing side, an outer crotch sheet lying on the non-skin-facing side and a plurality of strand- or string-like leg elastic elements interposed between the inner crotch and outer sheets.

(iii) A pair of the elastic lateral portions are formed by bonding the outer side zones and the inner side zones of the respective lateral portions via the lateral bond zones extending in the longitudinal direction and end segment bond zones extending along opposite end segments of the respective lateral portions in the transverse direction.

(iv) The lateral bond zones respective lie outboard of the respective leg elastic elements in the transverse direction at least in a midsection of the crotch region.

(v) At least one of the inner and outer crotch sheets is formed of a thermoplastic resin film.

(vi) Of the inner and outer crotch sheets, at least the inner crotch sheet is formed of a thermoplastic resin film and the surfaces to be bonded in the lateral bond zones and the end segment bond zones are of a thermoplastic resin film.

(vii) The inner side zones and the outer side zones of the respective lateral portions are bonded together via the associated bond zones and then partially folding the respective outer side zones outward in the transverse direction to form respective folded zones which are, in turn, bonded to the associated inner side zones via flap bond zones.

(viii) The inner side zones and the outer side zones of the respective lateral portions are bonded together via the associated bond zones and then partially folding the respective outer side zones outward in the transverse direction to form respective folded zones which are, in turn, bonded to the associated inner side zones via flap bond zones.

(ix) The folded back regions are fixed to the both laterals of the liquid-impervious sheet by means of bond zones.

(x) Outer side edges of the folded back regions are respectively shaped so as to curve concavely outward.

(xi) The leg elastic elements include first leg elastic elements extending in the longitudinal direction and second leg elastic elements curving convexly inward and wherein outer side edges of the respective folded back regions are shaped so as to curve concavely outward along the second leg elastic elements.

(xii) The outer side edges of the respective folded back regions are shaped so as to curve concavely outward and the lateral bond zones are spaced from the associated outer side edges and to surround the respective outer side edges.

According to the embodiments in the above (ii) to (xii), the advantageous effect(s) set forth at (a) is/are better ensured.

This application claims the benefit of Japanese Application Nos. 2011-019198 and 2011-265309, the entire disclosures of which are incorporated by reference herein.

The invention claimed is:

1. A disposable wearing article having a longitudinal direction, a transverse direction extending orthogonally to the longitudinal direction, said disposable wearing article comprising:
 a skin-facing side;
 a non-skin-facing side;
 a front waist region;
 a rear waist region; and
 a crotch region extending between the front and rear waist regions, and including an elastic waist panel defining the front and rear waist regions and a crotch chassis attached to the elastic waist panel to define respective portions of the front and rear waist regions and the crotch region,
wherein
the crotch chassis includes a liquid-impervious sheet having a main region and opposite lateral portions lying outboard of the main region in the transverse direction and provided with leg elastic elements extending in the longitudinal direction,
the opposite lateral portions respectively have
 fold lines extending in the longitudinal direction,
 outer side zones lying outboard of the respective fold lines in the transverse direction and
 inner side zones lying inboard of the respective fold lines in the transverse direction,
the outer side zones of the respective lateral portions are folded back inward and fixed to the associated inner side zones via associated bond zones extending in the longitudinal direction to form a pair of elastic lateral portions having folded back regions, respectively,
the leg elastic elements include first leg elastic elements extending in the longitudinal direction and second leg elastic elements curving convexly inward, and
outer side edges of the respective folded back regions are shaped so as to curve concavely outward along the second leg elastic elements.

2. The wearing article defined by claim 1, wherein
the liquid-impervious sheet is a laminated crotch sheet including an inner crotch sheet lying on the skin-facing side and an outer crotch sheet lying on the non-skin-facing side, and
the leg elastic elements are strand- or string-shaped leg elastic elements interposed between the inner and outer crotch sheets.

3. The wearing article defined by claim 2, wherein at least one of the inner and outer crotch sheets is formed of a thermoplastic resin film.

4. The wearing article defined by claim 2, wherein
the pair of the elastic lateral portions is formed by bonding the outer side zones and the inner side zones of the respective lateral portions via
lateral bond zones extending in the longitudinal direction, and
end segment bond zones extending along opposite end segments of the respective lateral portions in the transverse direction,
of the inner and outer crotch sheets, at least the inner crotch sheet is formed of a thermoplastic resin film, and
surfaces to be bonded in the lateral bond zones and the end segment bond zones are formed of a thermoplastic resin film.

5. The wearing article defined by claim 1, wherein the pair of the elastic lateral portions is formed by bonding the outer side zones and the inner side zones of the respective lateral portions via
lateral bond zones extending in the longitudinal direction, and
end segment bond zones extending along opposite end segments of the respective lateral portions in the transverse direction.

6. The wearing article defined by claim 5, wherein the lateral bond zones respective lie outboard of the respective leg elastic elements in the transverse direction at least in a mid-section of the crotch region.

7. The wearing article defined by claim 5, wherein the lateral bond zones are spaced from the associated outer side edges of the respective folded back regions and surround the associated outer side edges.

8. The wearing article defined by claim 1, wherein the inner side zones and the outer side zones of the respective lateral portions are bonded together via the associated bond zones and then partially folding the respective outer side zones outward in the transverse direction to form respective folded zones which are, in turn, bonded to the associated inner side zones via flap bond zones.

9. The wearing article defined by claim 1, wherein the main region of the crotch chassis is provided on the skin-facing side with a sheet-shaped bodily fluid absorbent structure comprising superabsorbent polymer particles wrapped with a liquid-pervious sheet.

10. The wearing article defined by claim 1, wherein the folded back regions are fixed to both the lateral portions of the liquid-impervious sheet by bond zones.

* * * * *